US005571161A

United States Patent [19]
Starksen

[11] Patent Number: 5,571,161
[45] Date of Patent: Nov. 5, 1996

[54] APPARATUS AND METHOD FOR IMPLANTING ELECTRICAL LEADS IN THE HEART

[76] Inventor: Niel F. Starksen, 12119 Edgecliff Pl., Los Altos, Calif. 94022

[21] Appl. No.: 422,182

[22] Filed: Apr. 12, 1995

[51] Int. Cl.[6] .................... A61M 25/10; A61M 25/00; A61M 25/01
[52] U.S. Cl. .................. 607/122; 607/119; 604/96; 604/161
[58] Field of Search .................. 607/119, 122; 128/772; 604/96, 161

[56] References Cited

U.S. PATENT DOCUMENTS

| 4,166,469 | 9/1979 | Littleford | 128/784 |
|---|---|---|---|
| 4,243,050 | 1/1981 | Littleford | 607/122 |
| 4,553,554 | 11/1985 | Lemole | 128/784 |
| 4,602,645 | 7/1986 | Barrington et al. | 607/123 |
| 4,848,344 | 7/1989 | Sos et al. | 128/772 |
| 4,924,881 | 5/1990 | Brewer | 128/785 |
| 4,991,578 | 2/1991 | Cohen | 128/419 D |
| 5,029,585 | 7/1991 | Lieber et al. | 128/642 |
| 5,099,839 | 3/1992 | Miyata et al. | 607/122 |
| 5,125,904 | 6/1992 | Lee | 604/161 |
| 5,129,404 | 7/1992 | Spehr et al. | 128/785 |
| 5,170,802 | 12/1992 | Mehra | 128/784 |
| 5,170,803 | 12/1992 | Hewson et al. | 128/786 |
| 5,174,303 | 12/1992 | Schroeppel | 128/786 |
| 5,183,464 | 2/1993 | Dubrul et al. | 604/96 |
| 5,190,528 | 3/1993 | Fonger et al. | 604/171 |
| 5,228,455 | 7/1993 | Barcel | 128/785 |
| 5,282,845 | 2/1994 | Bush et al. | 607/128 |
| 5,300,106 | 4/1994 | Dahl et al. | 607/119 |
| 5,308,325 | 5/1994 | Quinn et al. | 604/96 |
| 5,415,639 | 5/1995 | Vanden Einde et al. | 604/96 |

FOREIGN PATENT DOCUMENTS 219608   4/1987   European Pat. Off. .............. 607/122

OTHER PUBLICATIONS

Sutton et al, *The Foundations of Cardiac Pacing, PT. I: An Illustrated Practical Guide to Basic Pacing*, Futura Publishing Co., Inc., Mount Kisco, NY, C. 1991, pp. 187–196.

Product Brochure, Safesheath™, "Hemostatic Tear–Away Introducer System with Infusion Side Port," Pressure Products, Inc.

Cook Incorporated, "Technique for Catheter or Pacemaker Lead Introduction", *Peel Away* Flyer, Mar. 1979, p. 4.

*Primary Examiner*—William E. Kamm
*Assistant Examiner*—Carl H. Layno
*Attorney, Agent, or Firm*—Townsend and Townsend and Crew LLP

[57] ABSTRACT

A steerable guide catheter for the placement of electrical lead wires useful for cardiac pacemakers and other electrophysiology devices includes an atraumatic balloon at its distal end. The catheter has a proximal hemostatic seal and is axially splittable so that it may be removed over an electrical lead wire having an enlarged connector at its proximal end. The balloon is preferably asymmetrically mounted to permit such splitting.

18 Claims, 8 Drawing Sheets

2

APPARATUS AND METHOD FOR IMPLANTING ELECTRICAL LEADS IN THE HEART

BACKGROUND OF THE INVENTION

1. Field of the Invention

The present invention relates generally to the design and use of medical devices. More particularly, the present invention relates to a guide catheter which is useful for implanting cardiac pacemaker and defibrillation leads in the heart and coronary sinus.

Implantable cardiac pacemakers are widely used to treat a variety of cardiac conditions, particularly arrhythmias including both bradycardias and tachycardias. The use of pacemakers for defibrillation and other electrical therapies is also under development.

Implantable cardiac pacemakers require placement of electrical lead wires within the heart or coronary sinus, where the electrical leads may be connected to a remotely implanted pacemaking unit. Placement of the electrical lead wires can be accomplished either by open surgical techniques or by transvenous techniques. Of particular interest to the present invention, transvenous lead placement is accomplished by establishing percutaneous access to the venous system, typically via the subclavian vein, and passing the electrical lead to the desired target location within the heart, typically the right ventricular apex. The lead will include a self-anchoring mechanism at its distal end, typically a helix, screw, or tines, and the end of the lead wire can be engaged against and anchored in the endocardium.

Transvenous placement of the electrical leads for an implantable pacemaker can be problematic. At present, the leads are usually positioned using an internal stiffening stylet which is used to guide the distal end of the lead under fluoroscopic imaging. Since the leads lack column strength and there is substantial blood flow through the heart chambers, manipulating a lead is difficult and positioning of the lead is not always accurate. Thus, the physician must often disengage the lead anchor and reposition the lead one or more times before satisfactory placement is completed. It will be appreciated that such repositioning of the electrical lead can cause unnecessary trauma to the patient, with risk of causing arrhythmias and ventricular perforation.

The problem of positioning electrical leads for implantable cardiac pacemakers is partially addressed by electrical leads which have retractable lead anchors. See, for example, U.S. Pat. Nos. 5,129,404 and 4,924,881. Each of these patents discloses an electrical lead having a helical anchor which can be retracted within a body of the lead during introduction and initial placement of the lead within the heart. Alternatively, leads having a distal anchor protected by a soluble cover are available from Intermedics, Inc. Angleton, Tex. Such designs, however, can still be traumatic to the patient. The distal ends of the leads are blunt and can cause trauma when engaged against the endocardium. Moreover, the designs apparently do not allow for precise positioning since the patents contemplate that the anchor may be withdrawn back into the lead body one or more times for repositioning of the lead.

For these reasons, it would be desirable to provide improved methods and devices for implanting cardiac pacemaker lead wires within the heart. In particular, it would be desirable if such improved apparatus and methods addressed at least some of the deficiencies described above. More particularly, it would be desirable to provide apparatus and methods for accurately positioning electrical lead wires within the heart prior to implantation within the endocardium to reduce or eliminate the need for repositioning of the lead after implantation. It would be further desirable if the apparatus and methods were useful with conventional electrical leads so that the actual design of the pacemaker system need not be changed in any way.

2. Description of the Background Art

U.S. Pat. No. 4,166,469, describes an axially splittable introducer sheath which is used for introducing a pacemaker lead into the subclavian vein. The lead is pushed from the sheath to the heart. U.S. Pat. Nos. 5,129,404 and 4,924,881, described pacemaker lead wires having retractable helical anchors. U.S. Pat. No. 5,174,303, describes a pacemaker lead wire having a replaceable stylet with a distal sensor element. U.S. Pat. No. 5,228,455 describes a tool for implanting lead wires for pacemakers. Other cardiac electrodes and lead wires are described in U.S. Pat. Nos. 5,282,845; 5,228,455; 5,170,803; 5,170,802; 5,029,585; 4,991,578; and 4,553,554. Peel-away sheaths having a breakaway hemostasis value are manufactured by Pressure Products, Inc., Rancho Palos Verdes, Calif. and sold under the tradename SafeSheath™.

SUMMARY OF THE INVENTION

According to the present invention, a guide catheter is provided for the transvenous placement of intracardiac electrical lead wires useful for connection to implantable pacemakers, defibrillators, and other electrophysiology devices. The guide catheter is steerable (e.g. has a shaped distal end) to permit accurate positioning of its distal end at a target location within a heart chamber or vessel. Most commonly, the target location will be the right ventricular apex, but can also be the coronary sinus, tricuspid annulus, atrial appendage, atrial free wall (in patients with no atrial appendage), and the like. A balloon is provided at the distal end of the guide catheter to permit atraumatic engagement of the catheter against the endocardium at the target site. The guide catheter may be initially placed with or without use of a conventional J-tipped soft guide wire. After the distal end has been properly placed and placement confirmed, a conventional electrical lead wire may be introduced through the lumen of the guide catheter and engaged against the endocardium to anchor the lead in the conventional manner, e.g. using a distal helical or tins structure. By properly positioning the guide catheter prior to anchoring of the lead in the endocardium, the need to reposition the electrical lead after placement is reduced or eliminated.

In a particular aspect of the present invention, the guide catheter comprises a flexible tubular body having a proximal end, a distal end, and an axial lumen. A hub is secured to the proximal end and includes a primary access port which is aligned with the axial lumen of the flexible tubular body. A balloon is disposed at the distal end of the flexible tubular body, and suitable inflation means may be provided, such as an inflation lumen connected to an inflation port on the hub. In order to permit withdrawal of the guide catheter over the electrical lead wire (which typically has an enlarged proximal connector which mates with the implantable pacemaker), both the flexible tubular body and the hub will be splittable. In particular, the tubular body will have at least one axial separation line extending from the proximal end to the distal end. Similarly, the hub will be splittable so that it can be manually separated to remove both the hub and the tubular body. Additionally, the balloon will be attached to the distal end in such a way that axial separation of the body is possible. In the exemplary embodiment, the balloon is asymmetrically mounted at the distal end.

In another particular aspect of the present invention, a method for transvenous implantation of a lead wire in a heart chamber or vessel comprises introducing a guide catheter through the subclavian vein into the chamber vessel. A distal end of the guide catheter is positioned adjacent to a target location on the endocardium, and the lead wire is then introduced through a lumen of a guide catheter so that a terminal end engages the target location on the endocardium. After anchoring the lead wire, the guide catheter may be withdrawn over the lead wire, preferably by splitting the guide catheter as it is withdrawn over a connector on the lead wire. In the exemplary embodiment, a balloon near the distal end of the guide catheter is inflated prior to positioning in order to protect the endocardium from traumatic contact with the catheter.

DESCRIPTION OF THE SPECIFIC EMBODIMENT

Figure 1:
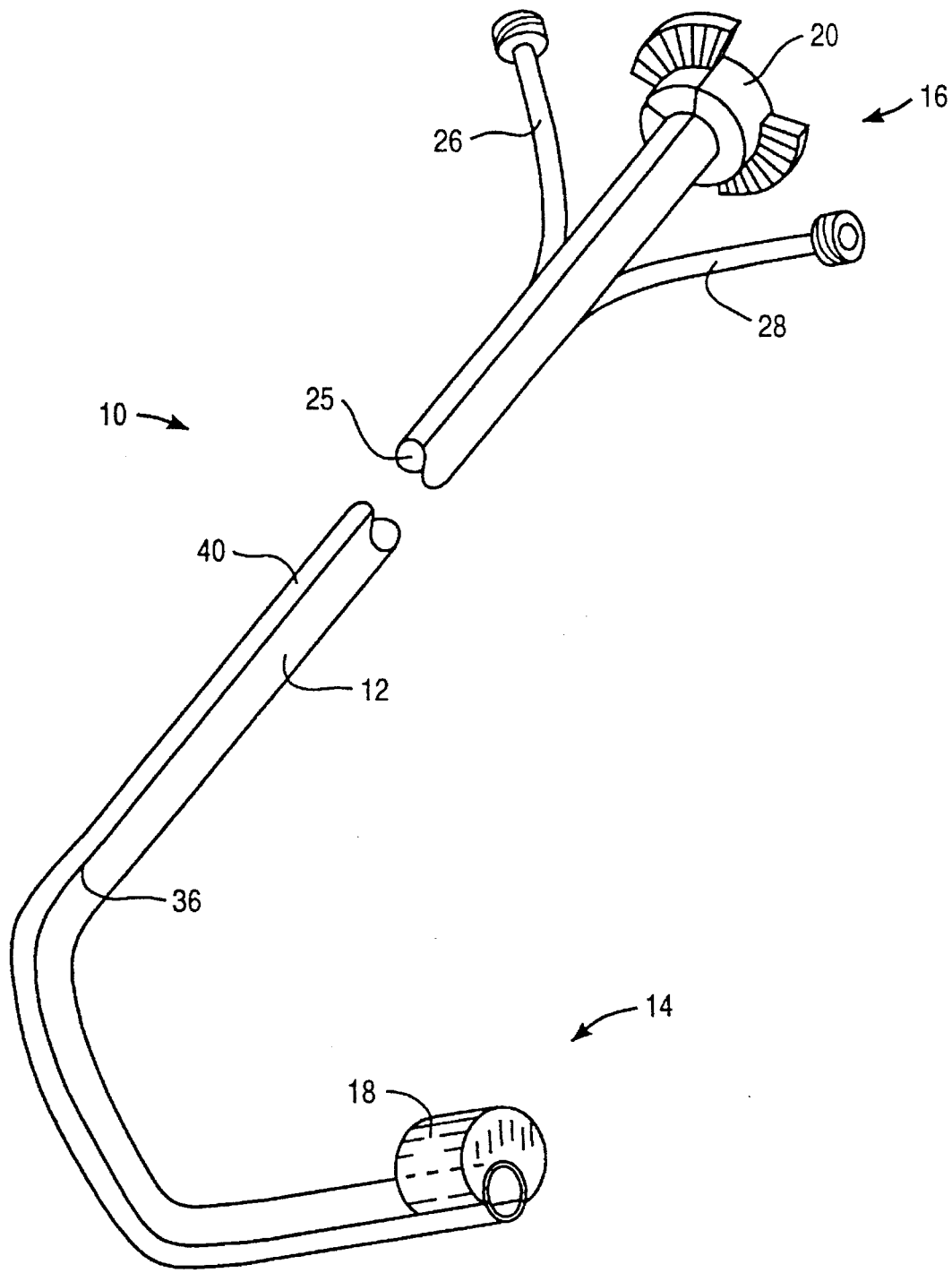
FIG. 1 is a perspective view of the guide catheter constructed in accordance with the principles of the present invention.

The present invention provides an intracardiac guide catheter useful for introducing implantable electrical leads to target sites within a heart chamber or vessel, including the atria, ventricles, coronary sinus, and the like. The electrical leads, in turn, may be used for connection to implantable pacemakers, defibrillators, or other electrophysiology devices which require stimulation and/or monitoring of the endocardium or other surfaces in and around the heart. In addition to electrical lead wire placement, the guide catheter of the present invention could find use whenever transvenous access to a heart chamber or associated heart vessel is desired.

The guide catheter will comprise a flexible tubular body having a proximal end and a distal end. A hub will be secured to the proximal end of the flexible tubular body and will provide at least one axial access port aligned with an axial lumen of the flexible tubular body. Typically, a hemostatic valve or element will be located within the proximal hub, usually being a penetrable diaphragm which permits passage of the electrical lead wire, as will be described in more detail below.

The flexible tubular body will typically have a length in the range from about 40 cm to 100 cm, usually having a length in the range of about 40 cm to 60 cm. The inner diameter of the tubular body will be sufficient to accommodate a cardiac pacemaker lead (usually with the terminal electrode tip retracted or folded), typically being in the range from about 6.5 French (F; 1 F=0.33 mm) to 12 F, usually being in the range from about 7.5 F to 10 F.

The flexible tubular body may be composed of any physiologically compatible material, typically being a thin-walled flexible plastic, such as a polyethylene, polytetrafluorethylene (PTFE), fluorinated ethylene-propylene, or the like. The tube may be extruded by conventional means and will include at least one thin or weakened axial groove or line extending from the proximal end to the distal end. The weakened line may be formed during the extrusion process using conventional techniques.

The proximal hub will also be weakened along at least one line, preferably along at least two lines, so that it may be split in a manner that will tear apart the flexible tubular body along its entire length to permit withdrawal of the guide catheter over an underlying element having an enlarged proximal end, such as an electrical lead wire having an enlarged proximal connector.

The guide catheter will also have a balloon disposed at the distal end of the flexible tubular body. The balloon will be inflatable from an inflation port which is typically connected to an inflation lumen running over at least a distal portion of the flexible tubular body. This will be described below, the inflatable balloon is provided to protect the distal end from injuring the endocardium when the guide catheter is introduced to a heart chamber. The balloon may also be used as a flow direction device when the catheter is being introduced to the target location within the heart. The balloon may cover all or a portion of the circumference of the distal end of the flexible tubular body, preferably covering an arc from about 225° to 350° of the circumference. The fully inflated diameter of the balloon will typically be from 5 mm to 10 mm over the asymmetric portion of the circumference where it is located.

Figure 2:
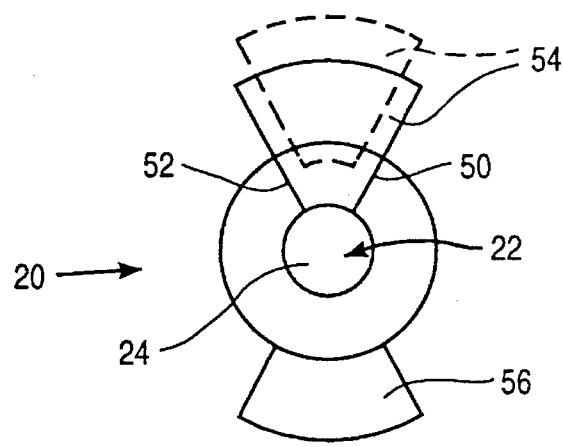
FIG. 2 is a proximal end view of the catheter of FIG. 1, with axial splitting of the hub shown in broken line.
Figure 3:
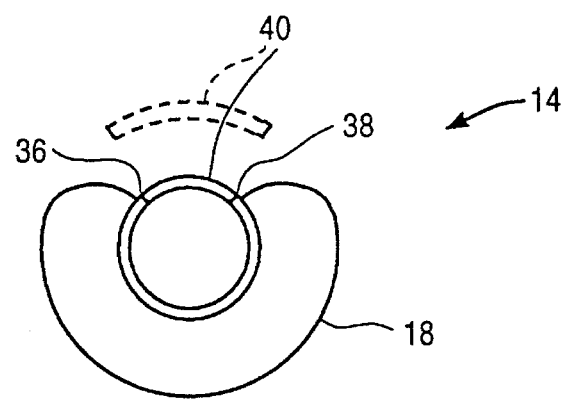
FIG. 3 is a distal end view of a guide catheter of FIG. 1, with axial splitting of the flexible tubular body and balloon inflation shown in broken line.

Referring now to FIGS. 1–3, an exemplary guide catheter 10 includes a flexible tubular body 12 having a distal end 14 and a proximal end 16. A balloon 18 is mounted on the distal end of the flexible tubular body 12, and a hub 20 is mounted on the proximal end of the flexible tubular body. The hub 20 includes an axial port 22 (FIG. 2) having a hemostatic diaphragm 24 positioned therein. The port 22 is aligned with axial lumen 25 of the flexible tubular body 12 so that an electrical lead or other device passed through the port will be directed out of the distal end 14 of the catheter 10. The catheter 10 further includes a perfusion connector 26 which can be used for introducing contrast media through the catheter 10 during a procedure. An inflation connector 28 is also provided and connected to the balloon 18 through an inflation lumen (not shown) which runs through the flexible tubular body 12.

As best seen in FIG. 3, the flexible tubular body 12 includes a pair of circumferentially spaced-apart axial separation lines 36 and 38. The separation lines are spaced apart by an arc of 120° and run parallel to each other over the flexible tubular body 12. The separation lines 36 and 38 thus define a removable strip 40 which can be split from the flexible tubular body 12, as described in more detail below.

As also best seen in FIG. 3, the balloon 18 is asymmetrically mounted over the distal end 14 of the flexible tubular body 12. In this way, it leaves the strip 40 to be removed from the remaining portion of the body 12, as illustrated in broken line.

Referring now to FIG. 2, hub 20 also includes a pair of axial separation lines 50 and 52. The separation lines 50 and 52 may be formed during injection molding or other fabrication technique for the hub 20. The separation lines 50 and 52 are aligned generally with separation lines 36 and 38 on the flexible tubular body, and manual splitting of tab 54 from tab 56 on the hub (as shown in broken line in FIG. 2) will result in separation of both the hub 20 and the strip 40 to permit withdrawal of the guide catheter over a device which is received within the axial lumen 26.

Figure 5:
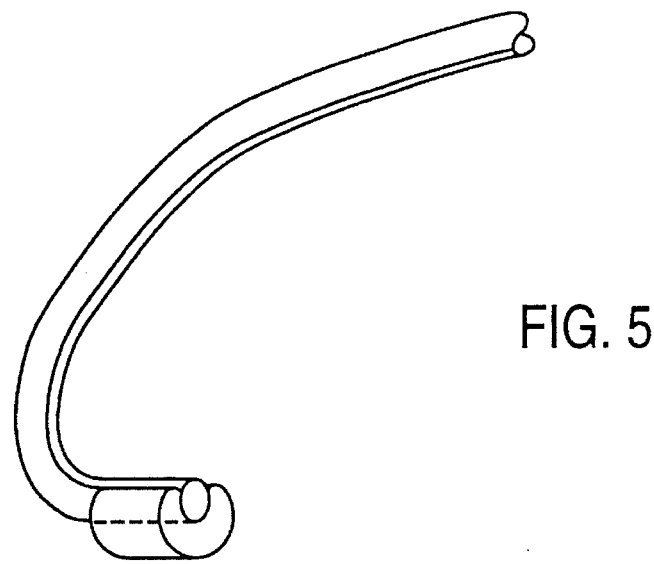
FIG. 5 illustrates an alternative distal end of the guide catheter of FIG. 1, intended for introduction to the coronary sinus.
Figure 6:
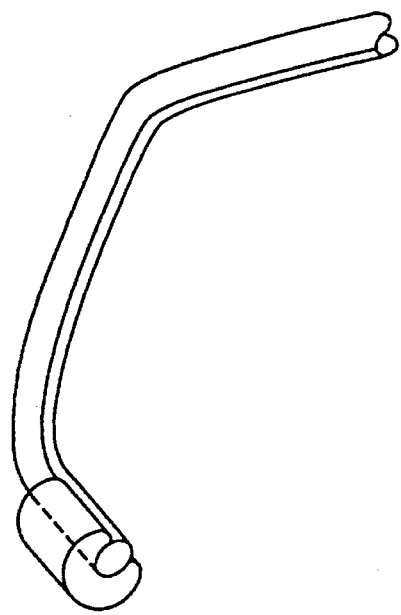
FIG. 6 illustrates an alternative construction of the distal end of the guide catheter of FIG. 1, intended for introduction to the tricuspid annulus.
Figure 7:
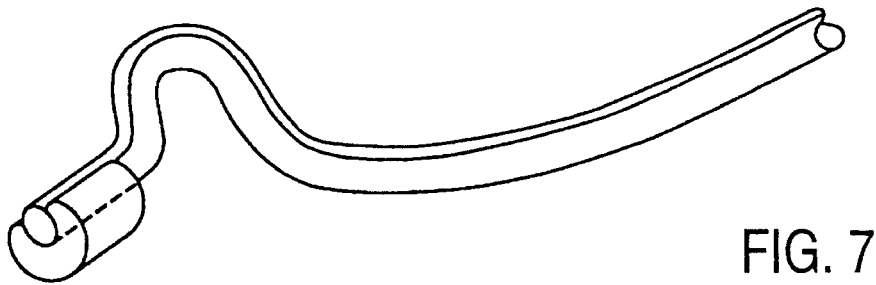
FIG. 7 illustrates an alternative construction of the distal end of the guide catheter of FIG. 1, intended for introduction to the atrial appendage or right atrial free wall.

Catheter 10 has a curved distal end, as best seen in FIG. 1. The particular geometry shown in FIG. 1 is intended for introduction to the right ventricular apex of the heart, as described in more detail with reference to FIGS. 8A–8E below. The geometry of the distal end can be varied for other target locations. For example, the geometry for introduction into the coronary sinus is illustrated in FIG. 5. The geometry for introduction to the tricuspid annulus is illustrated in FIG. 6. The geometry for introduction to the atrial appendage or atrial free wall is illustrated in FIG. 7.

Figure 4:
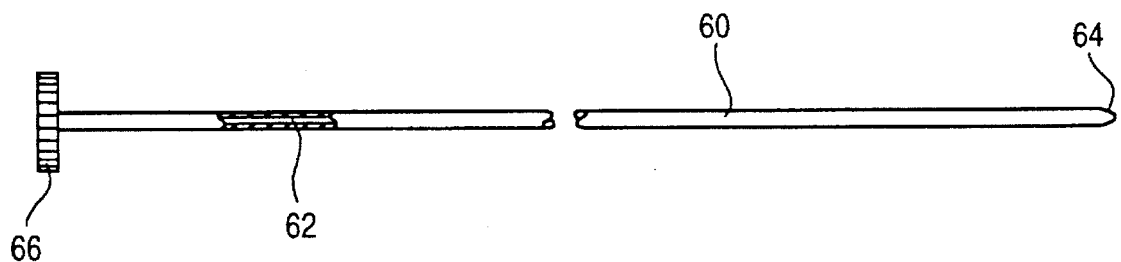
FIG. 4 illustrates a stylet useful for introducing the guide catheter of FIG. 1 to a target location within a heart chamber or vessel.

FIG. 4 illustrates an introduce stylet/dilator 60 intended for removable insertion through the catheter 10. The stylet will straighten the curved geometry and facilitate introduction of the guide catheter over a guide wire, as described below. In particular, the stylet 16 includes a guide wire lumen 62 extending from a tapered distal end 64 to a proximal handle 66. After the guide catheter is introduced to the desired target location, the stylet can be removed to permit full access to the central lumen.

Figure 8A:
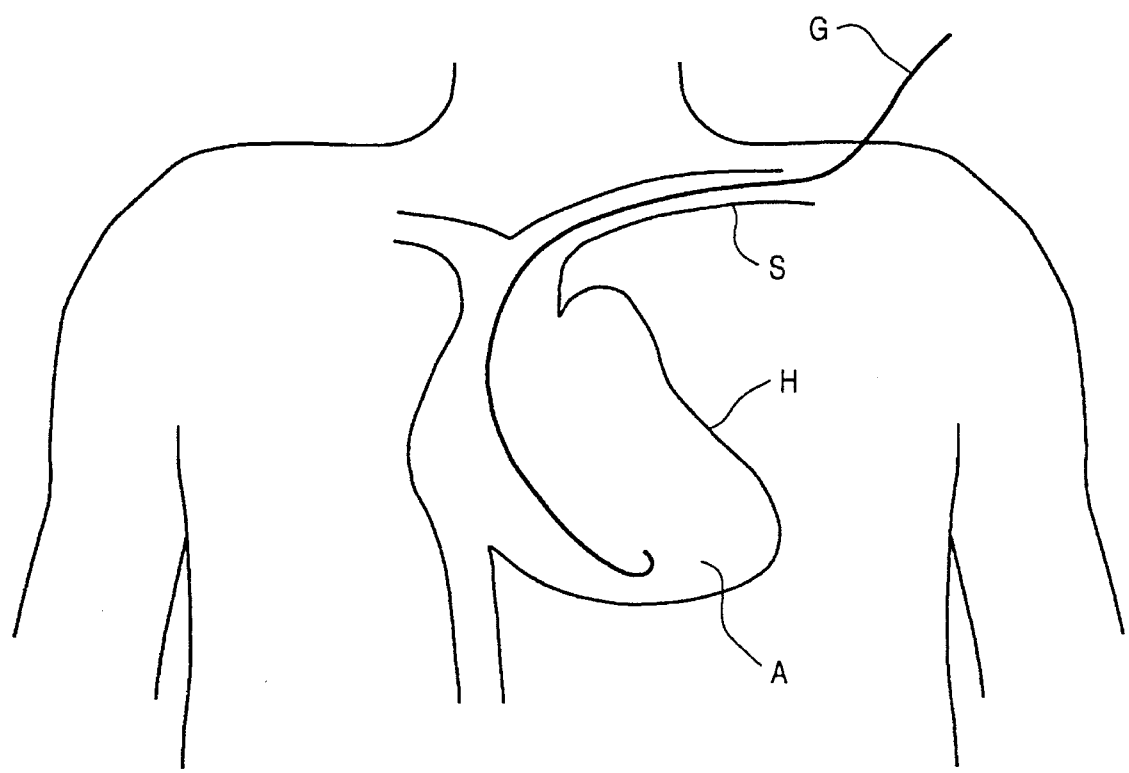
FIGS. 8A–8E illustrate the use of the guide catheter of FIG. 1 for introducing an electrical lead wire to the right ventricular apex, according to the method of the present invention.

Referring now to FIGS. 8A–8E, use of the guide catheter 10 for introducing an electrical lead to the right ventricular apex A of the heart H will be described. Initially, a guide wire G is percutaneously introduced through the subclavian vein S to the inferior-vena cava or right atrium in the convention manner. Typically, the guide wire G is introduced using a hollow needle which is then removed from the guide wire after the guide wire is properly positioned. The guide wire is shown in its proper position in the right atrium near the inferior vena cava (FIG. 8A).

Figure 8B:
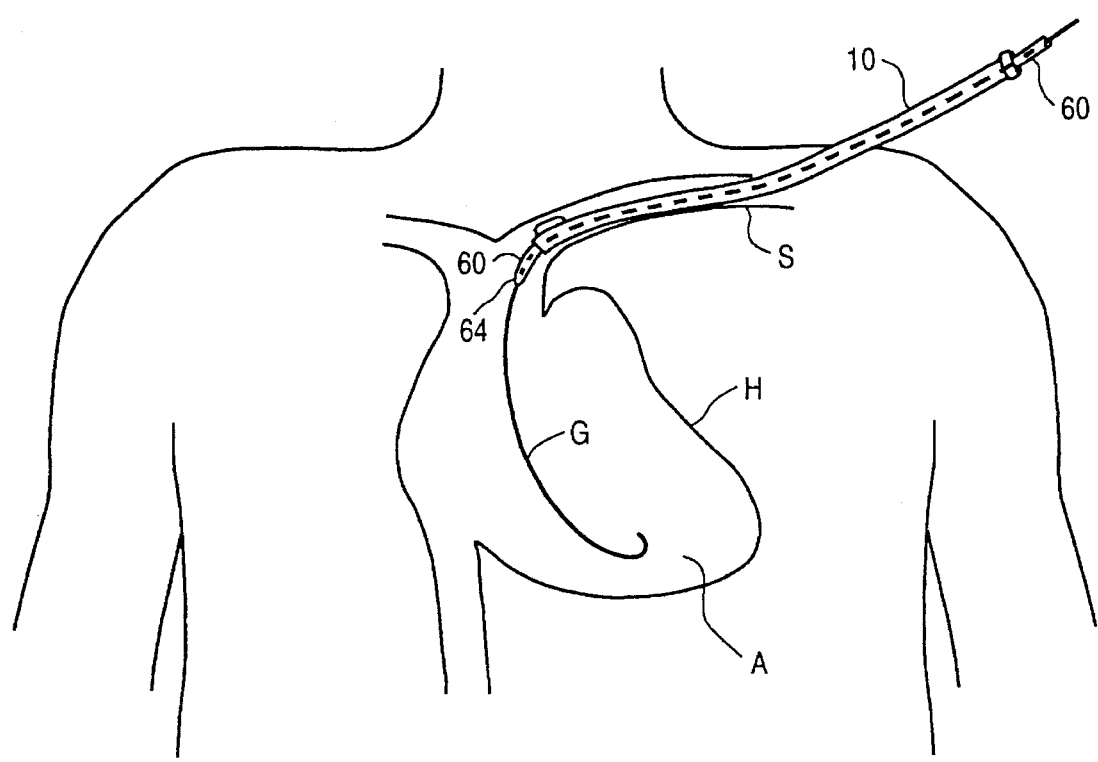

Referring now to FIG. 8B, the guide catheter 10 having stylet 60 in place is introduced over the guide wire G. The tapered distal end 64 of the stylet facilitates introduction of the guide catheter through the percutaneous access tract into the subclavian vein S. The guide catheter 10 can then be advanced until its distal end enters the right atrium.

Figure 8C:
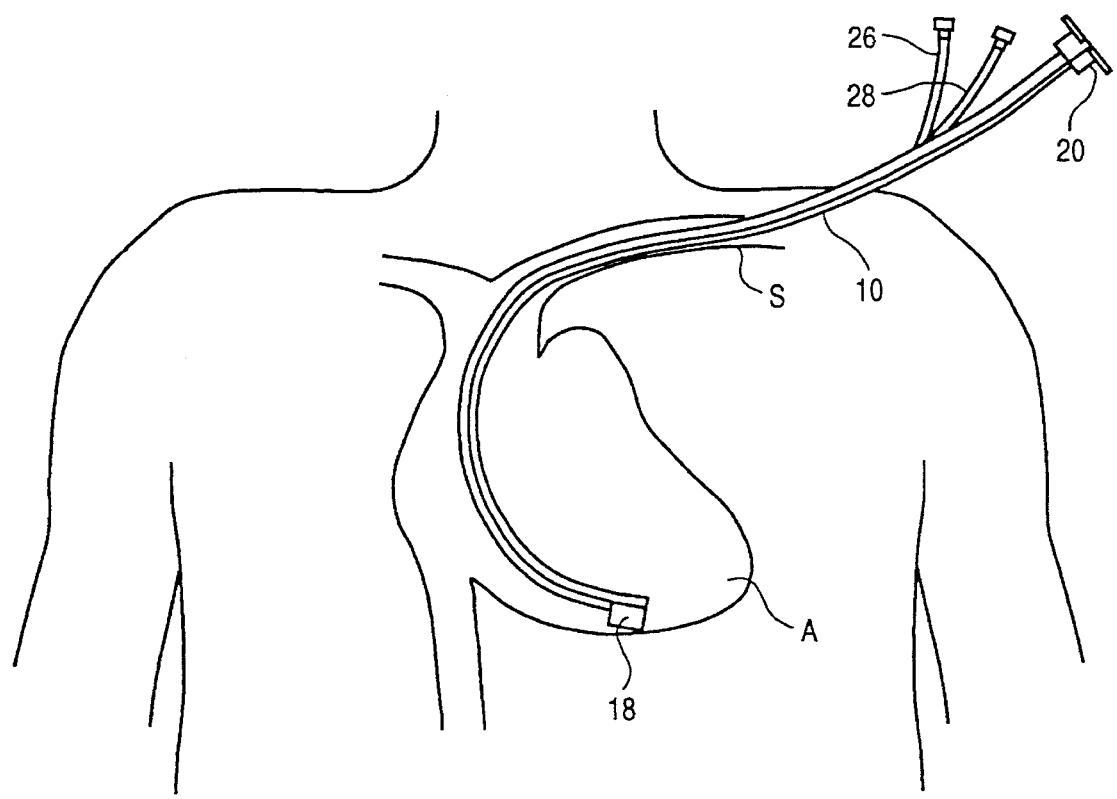

After the guide catheter 10 is positioned within the right atrium, the stylet dilator 60 is removed with the guide wire G optionally left in place, and balloon 18 is inflated, as illustrated in FIG. 8C. With the balloon inflated, the distal end of the guide catheter 10 can be moved (over the guide wire G if left in place) until it is properly positioned adjacent a target location, in this case, the right ventricular apex.

After the distal end of the guide catheter 10 is properly positioned, the guide wire G is removed and a self-anchoring electrical lead E is introduced through the guide catheter so that an anchor AN at its distal end can be engaged against and into the endocardium. The anchor AN may be in the form of a helix, a tine structure, or any other conventional self-anchoring mechanism.

Figure 8D:
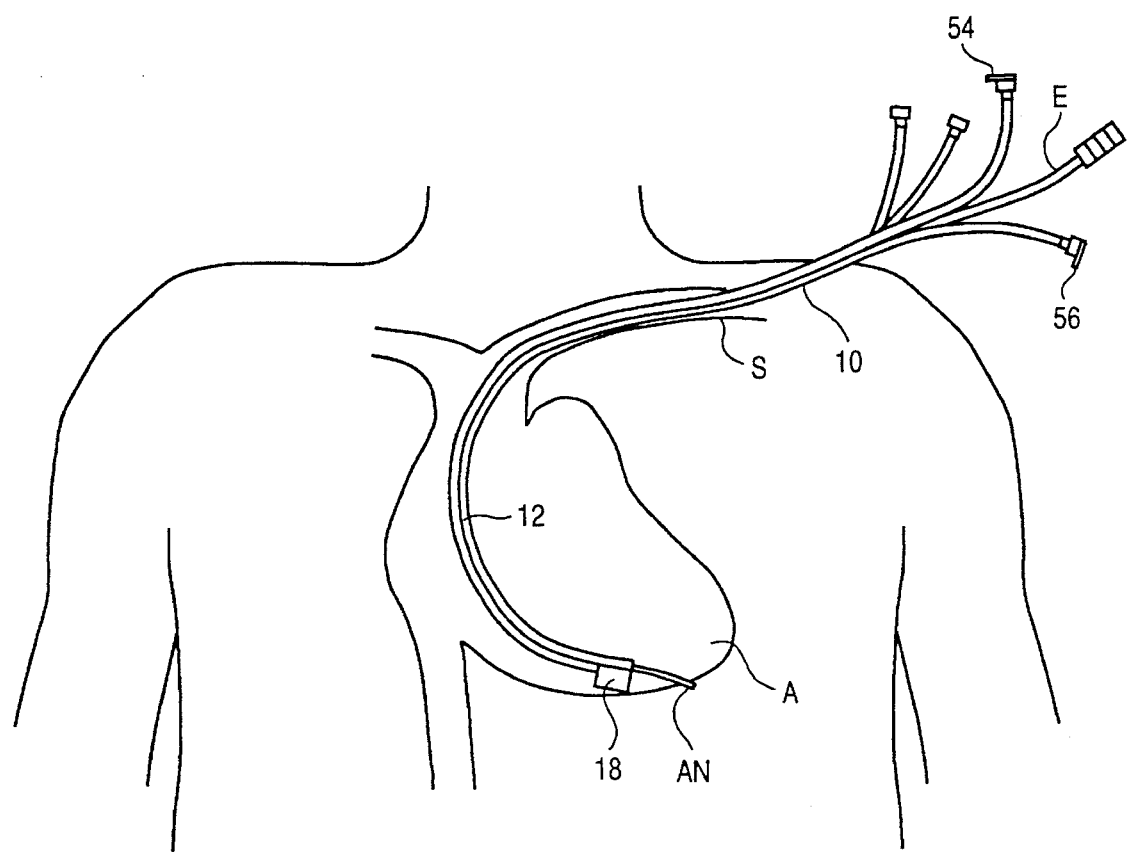
Figure 8E:
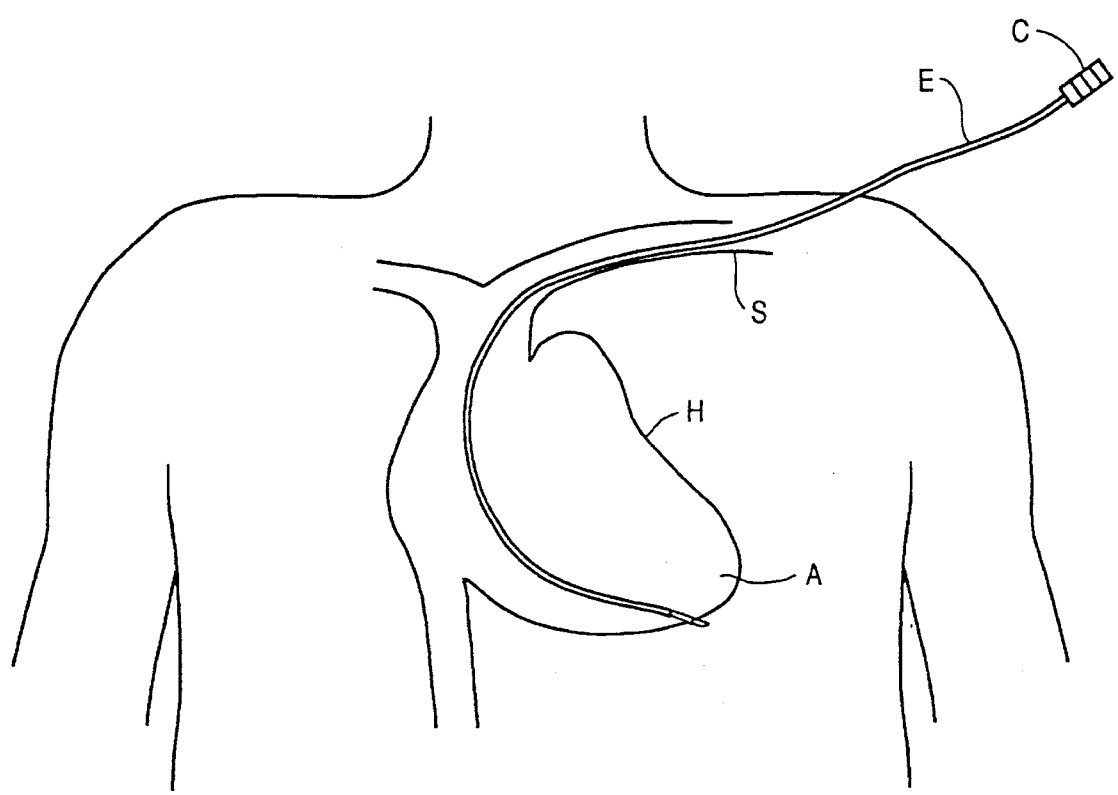

After confirming that the electrical lead is properly positioned, the catheter 10 will be withdrawn by pulling apart tabs 54 and 56, as illustrated in FIG. 8D. Separation of the hub 20 and the flexible tubular body 12 permits withdrawal of the catheter 10 over the enlarged connector C at the proximal end of the electrical lead wire E. After the catheter 10 has been completely withdrawn, the electrical lead remains in place, as illustrated in FIG. 8E. The connector C can then be connected with an implantable pacemaker according to conventional procedures.

Although the foregoing invention has been described in some detail by way of illustration and example, for purposes of clarity of understanding, it will be obvious that certain changes and modifications may be practiced within the scope of the appended claims.

What is claimed is:

1. A steerable guide catheter comprising:

a flexible tubular body having a proximal end, a distal end, an axial lumen, and at least one axial separation line extending from the proximal end to the distal end;

a hub having a hemostatic seal secured to the proximal end of the flexible tubular body, said hub having a primary access port which is axially aligned with the axial lumen of the flexible tubular body, wherein the hub has at least one weakened axial line so that it may be manually separated along said at least one axial line; and a balloon at the distal end of the flexible tubular body, said balloon being attached to the flexible tubular body in a manner which permits axial separation of the body.

2. A guide catheter as in claim 1, wherein the flexible tubular body has a length in the range from 40 cm to 100 cm and a lumen diameter in the range from about 6.5 F to 12 F.

3. A guide catheter as in claim 1, wherein a second axial separation line is formed on the flexible tubular body parallel to said at least one axial separation line.

4. A guide catheter as in claim 3, wherein the hub has two weakened axial lines in alignment with the two axial separation lines on the flexible tubular body.

5. A guide catheter as in claim 4, wherein the two of axial separation lines are separated by an arc in the range from 10° to 135°.

6. A guide catheter as in claim 5, wherein the balloon is asymmetrically disposed on the flexible tubular body so that it does not extend into the 10° to 135° region between the separation lines.

7. A guide catheter as in claim 6, further comprising an inflation port on the hub and an inflation lumen in the flexible body, wherein the port is connected to the lumen and the lumen is connected to the balloon.

8. A guide catheter as in claim 1, further comprising a contrast media port on the hub.

9. An improved guide catheter of the type including an elongated flexible body having a proximal end and a distal end and a hub secured to the proximal end, wherein the improvement comprises a balloon mounted on the flexible body near the distal end thereof and means for opening an axial passage along the entire length of the flexible body and hub so that the catheter can be withdrawn over a proximal structure on a device disposed within a body lumen.

10. A method for the guided transvenous implantation of a lead wire in a heart chamber, said method comprising:

introducing a steerable guide catheter through the subclavian vein to the heart chamber;

positioning a distal end of the guide catheter adjacent to a target location on the endocardium;

introducing the lead wire through a lumen of the guide catheter so that a terminal of the lead wire engages the target location on the endocardium; and withdrawing the guide catheter over the lead wire to leave the lead wire in place.

11. A method as in claim 10, further comprising inflating a balloon near the distal end of the guide catheter prior to the step of positioning, wherein the balloon protects the endocardium from traumatic contact with the catheter.

12. A method as in claim 10, wherein the guide catheter is withdrawn by splitting the catheter along at least one axial line to permit passage of the catheter by a connector on the proximal end of the lead wire.

13. A method as in claim 10, wherein the guide catheter is introduced over a guide wire.

14. A method as in claim 13, wherein a stylet is placed in the lumen of the guide catheter while the guide catheter is introduced over the guide wire.

15. An improved method for implanting a lead wire in a heart chamber wherein the lead wire is transvenously implanted through the subclavian vein, wherein the improvement comprises positioning a guide catheter from a percutaneous access site to a target site within the heart chamber and introducing the lead wire through a lumen of the guide catheter.

16. An improved method as in claim 15, wherein the improvement further comprises withdrawing the guide catheter over the lead wire after said lead wire has been implanted.

17. An improved method as in claim 16, wherein the guide catheter is withdrawn by axially splitting the catheter.

18. An improved method as in claim 15, wherein the improvement further comprises inflating a balloon on the guide catheter to protect the endocardium, where said inflating step is performed after positioning the guide catheter and before implanting the lead wire.

* * * * *